United States Patent [19]

Medero

[11] Patent Number: 5,577,508

[45] Date of Patent: Nov. 26, 1996

[54] DETERMINATION OF OSCILLOMETRIC BLOOD PRESSURE BY LINEAR APPROXIMATION

[75] Inventor: Richard Medero, Tampa, Fla.

[73] Assignee: Johnson & Johnson Medical, Inc., New Brunswick, N.J.

[21] Appl. No.: 372,573

[22] Filed: Jan. 13, 1995

[51] Int. Cl.$^6$ .................................................. A61B 05/00
[52] U.S. Cl. .......................................... 128/681; 128/682
[58] Field of Search .................................. 188/672, 677, 188/680.3, 687

[56] References Cited

U.S. PATENT DOCUMENTS

| | | | |
|---|---|---|---|
| 4,349,034 | 9/1982 | Ramsey, III | 128/681 |
| 4,360,029 | 11/1982 | Ramsey, III | 128/681 |
| 4,461,266 | 7/1984 | Hood, Jr. et al. | 128/681 |
| 4,543,962 | 10/1985 | Medero et al. | 128/682 |
| 4,546,775 | 10/1985 | Medero | 128/681 |
| 4,627,440 | 12/1986 | Ramsey, III et al. | 128/682 |
| 4,638,810 | 1/1987 | Ramsey, III et al. | 128/681 |
| 4,754,761 | 7/1988 | Ramsey, III et al. | 128/683 |
| 4,774,960 | 10/1988 | Arnold et al. | 128/681 |
| 4,796,184 | 1/1989 | Bahr et al. | 128/681 |
| 4,889,133 | 12/1989 | Nelson et al. | 128/681 |
| 4,917,098 | 4/1990 | Murase | 128/681 |
| 4,926,873 | 5/1990 | Frankenreiter | 128/681 |
| 4,949,710 | 8/1990 | Dorsett et al. | 128/680 |
| 4,984,577 | 1/1991 | Frankenreiter | 128/681 |
| 5,052,397 | 10/1991 | Ramsey, III et al. | 128/682 |
| 5,054,495 | 10/1991 | Uemura et al. | 128/680 |
| 5,103,833 | 4/1992 | Apple | 128/687 |
| 5,170,795 | 12/1992 | Ramsey, III et al. | 128/682 |
| 5,218,968 | 6/1993 | Apple | 128/687 |
| 5,253,648 | 10/1993 | Walloch | 128/681 |
| 5,261,413 | 11/1993 | Kawahara | 128/682 |
| 5,280,790 | 1/1994 | Brooks | 128/681 |
| 5,311,872 | 5/1994 | Apple | 128/687 |

*Primary Examiner*—Angela D. Sykes
*Assistant Examiner*—Robert L. Nassei, Jr.
*Attorney, Agent, or Firm*—Woodcock Washburn Kurtz Mackiewicz & Norris

[57] ABSTRACT

An automated sphygmomanometer which models the oscillometric envelope as two lines through the points defined by pressure and amplitude which are determined during the oscillometric blood pressure determination. One of the lines is the best fit through the points on the low pressure (diastolic) side of the oscillometric envelope, while the other line is the best fit through the points on the high pressure (systolic) side of the oscillometric envelope. The dividing point for the low and high pressure sides is chosen as the point where the best fit line through the points on one side and the best fit line through the points on the other side have the greatest amplitude at the point of intersection. The result is a linear approximation of the oscillometric envelope by two lines forming a triangle with the baseline. A second pass is preferably performed to improve the linear approximation by eliminating points with oscillation amplitudes that are outside of the area of interest. The best fit lines are then recalculated from the remaining points, and the points where the best fit lines intersect (or some function thereof) is then used as MAP and for determining the systolic and diastolic pressures. The resulting method for calculating systolic, MAP, and diastolic pressures is less sensitive to erroneous oscillation amplitudes since all points in the area of interest along the oscillometric envelope are weighted equally.

10 Claims, 4 Drawing Sheets

DETERMINATION OF OSCILLOMETRIC BLOOD PRESSURE BY LINEAR APPROXIMATION

FIELD OF THE INVENTION

This invention relates to automated blood pressure monitoring, and more particularly, to automated blood pressure monitors that utilize a pneumatic cuff for accomplishing a sphygmomanometric measurement on a patient.

BACKGROUND OF THE INVENTION

The sphygmomanometric class of automated blood pressure monitors employs an inflatable cuff to exert controlled counter-pressure on the vasculature of a patient. One large class of such monitors, exemplified by that described in U.S. Pat. Nos. 4,349,034 and 4,360,029, both to Maynard Ramsey, III and commonly assigned herewith and incorporated by reference, employs the oscillometric methodology. In accordance with the Ramsey patents, an inflatable cuff is suitably located on the limb of a patient and is pumped up to a predetermined pressure above the systolic pressure. Then, the cuff pressure is reduced in predetermined decrements, and at each level, pressure fluctuations are monitored. The resultant arterial pulse signals typically consist of a DC voltage with a small superimposed variational component caused by arterial blood pressure pulsations (referred to herein as "oscillation complexes" or just simply "oscillations"). The oscillation complexes typically have amplitudes which are typically about one percent that of the arterial pulse signals. After suitable filtering to reject the DC component and to provide amplification by a scale factor, peak pulse amplitudes (PPA) above a given base-line are measured and stored. As the decrementing continues, the peak amplitudes will normally increase from a lower level to a relative maximum, and thereafter will decrease. These amplitudes form an oscillometric envelope for the patient. The lowest cuff pressure at which the oscillations have a maximum value has been found to be representative of the mean arterial pressure ("MAP"). Systolic and diastolic pressures can be derived either as predetermined fractions of MAP, or by more sophisticated methods of direct processing of the oscillation complexes.

The step deflation technique as set forth in the Ramsey patents is the commercial standard of operation. A large percentage of clinically acceptable automated blood pressure monitors utilize the step deflation rationale. When in use, the blood pressure cuff is placed on the patient and the operator usually sets a time interval, typically from 1 to 90 minutes, at which blood pressure measurements are to be made. The noninvasive blood pressure ("NIBP") monitor automatically starts a blood pressure determination at the end of the set time interval.

FIG. 1 illustrates a simplified version of the oscillometric blood pressure monitor described in the aforementioned Ramsey patents. In FIG. 1, the arm 100 of a human subject is shown wearing a conventional flexible inflatable and deflatable cuff 101 for occluding the brachial artery when fully inflated. As the cuff 101 is deflated using deflate valve 102 having exhaust 103, the arterial occlusion is gradually relieved. The deflation of cuff 101 via deflate valve 102 is controlled by microprocessor 107 via control line 108.

A pressure transducer 104 is coupled by a duct 105 to the cuff 101 for sensing the pressure therein. In accordance with conventional oscillometric techniques, pressure oscillations in the artery are sensed by changes in the counter-pressure of the cuff 101, and these pressure oscillations are converted into an electrical signal by transducer 104 and coupled over path 106 to microprocessor 107 for processing. In addition, a source of pressurized air 109 is connected via a duct 110 through an inflate valve 111 and a duct 112 to the pressure cuff 101. The inflate valve 111 is electrically controlled through a connection 113 from the microprocessor 107. Also, the deflate valve 102 is connected by duct 114 via a branch connection 115 with the duct 112 leading to cuff 101.

Microprocessor 107 processes the signals from pressure transducer 104 to produce blood pressure data and to reject artifact data as described in the afore-mentioned Ramsey '029 and '034 patents. However, the blood pressure also can be determined in accordance with the teachings of Medero et al. in U.S. Pat. No. 4,543,962, of Medero in U.S. Pat. No. 4,546,775, of Hood, Jr. et al. in U.S. Pat. No. 4,461,266, of Ramsey, III et al. in U.S. Pat. No. 4,638,810, of Ramsey, III et al. in U.S. Pat. No. 4,754,761, of Ramsey, III et al. in U.S. Pat. No. 5,170,795, and of Ramsey, III et al. in U.S. Pat. No. 5,052,397, all of which are commonly assigned herewith and the disclosures of which are hereby incorporated by reference. Any of these known techniques are used to determine the quality of the oscillation complexes received at each level so that the blood pressure determination is made using actual blood pressure data and not artifacts.

During operation of the apparatus illustrated in FIG. 1, it is assumed that air under pressure to about 8–10 p.s.i. is available in the source of pressurized air 109. When it is desired to initiate a determination of blood pressure, the microprocessor 107 furnishes a signal over path 113 to open the inflate valve 111. The deflate valve 102 is closed. Air from the source 109 is communicated through inflate valve 111 and duct 112 to inflate the cuff 101 to a desired level, preferably above the estimated systolic pressure of the patient. Microprocessor 107 responds to a signal on path 106 from the pressure transducer 104, which is indicative of the instantaneous pressure in the cuff 101, to interrupt the inflation of the cuff 101 when the pressure in the cuff 101 reaches a predetermined value above the estimated systolic pressure of the patient. Such interruption is accomplished by sending a signal over path 113 instructing inflate valve 111 to close. Once inflate valve 111 has been closed, the blood pressure measurement can be obtained by commencing a deflate routine.

Actual measurement of the blood pressure under the control of the microprocessor 107 and the deflate valve 102 and as sensed by pressure transducer 104 can be accomplished in any suitable manner such as that disclosed in the aforementioned patents. At the completion of each measurement cycle, the deflate valve 102 can be re-opened long enough to relax the cuff pressure substantially completely via exhaust 103. Thereafter, the deflate valve 102 is closed for the start of a new measurement cycle.

Accordingly, when a blood pressure measurement is desired, the inflate valve 111 is opened while the cuff pressure is supervised by pressure transducer 104 until the cuff pressure reaches the desired level. The inflate valve 111 is then closed. Thereafter, the deflate valve 102 is operated using signal 108 from microprocessor 107 and the blood pressure measurement taken.

Prior art FIG. 2 illustrates a pressure versus time graph illustrating a conventional cuff step deflation and measurement cycle for a conventional NIBP monitor. As illustrated, the cuff 101 is inflated to a pressure above the systolic pressure, and the cuff 101 is then deflated in steps of equal duration of about 8 mm Hg per step. A timeout duration d is provided at each step during which the signal processing circuitry searches for oscillation complexes in accordance with the techniques described in the afore-mentioned commonly assigned patents. At the end of timeout duration d, the cuff pressure is decremented even if no oscillation complex is detected. This process of decrementing the pressure and searching for oscillation complexes is repeated at least until MAP and/or the oscillometric envelope 200 may be determined. The entire blood pressure determination process is repeated at intervals set by the user or some other predetermined intervals.

As shown in FIG. 2, the patient's arterial blood pressure forms an oscillometric envelope 200 comprised of a set of oscillation amplitudes measured at the different cuff pressures. From oscillometric envelope 200, systolic, MAP and diastolic blood pressures are typically determined. Typically, these blood pressure determinations require that the maximum amplitude (MAP) be known. Indeed, as noted above, MAP is found at the lowest cuff pressure at which the oscillations have a maximum amplitude. From this maximum amplitude, amplitudes for the systolic and diastolic pressures are calculated using known equations and the corresponding cuff pressures are determined and displayed as the systolic and diastolic pressures. MAP is then computed and displayed from amplitudes and pressures on the low (diastolic) and high (systolic) pressure sides of the known maximum amplitude.

Unfortunately, this method for calculating MAP is somewhat sensitive to erroneous high oscillation amplitudes which are mistakenly treated as corresponding to the MAP pressure. This is so because a single point is used to define MAP and systolic pressures, and only one or two points are used to define diastolic pressure. An envelope analysis technique is desired which is less sensitive to erroneous oscillation amplitudes and can thus provide a more accurate MAP determination.

It is, accordingly, a primary object of the present invention to provide an oscillometric envelope analysis method which is less sensitive to erroneous oscillation amplitudes.

It is a further object of the present invention to weigh all points along the oscillometric envelope equally and to use all measured points in the MAP determination.

It is also an object of the present invention to provide a linear approximation technique for determining the oscillometric envelope and simplifying signal processing requirements.

SUMMARY OF THE INVENTION

The above objects have been met in accordance with the present invention by providing an automated sphygmomanometer which models the oscillometric envelope as two lines through the points defined by pressure and amplitude which are determined during the oscillometric blood pressure determination. One of the lines is the best fit through the points on the low pressure side of the oscillometric envelope, while the other line is the best fit through the points on the high pressure side of the oscillometric envelope. The dividing point for the low and high pressure sides is chosen as the point where the best fit line through the points on one side and the best fit line through the points on the other side have the greatest amplitude at the point of intersection. The result is a linear approximation of the oscillometric envelope by two lines forming a triangle with the baseline.

Preferably, a second pass is performed to improve the linear approximation by eliminating points with oscillation amplitudes that are outside of the area of interest (e.g., are at pressures above systolic or below diastolic) such as points that have oscillation amplitudes less than half of the maximum determined in the first pass. The best fit lines are then recalculated from the remaining points, and the points (or some function of the points) where the best fit lines intersect is then used as MAP and as the maximum amplitude for the determination of the systolic and diastolic pressures. Of course, subsequent passes may be taken until all remaining points are within a certain tolerance. The best fit line through the points on the diastolic side of the oscillometric envelope is then used to calculate the diastolic pressure, while the best fit line through the points on the systolic side of the oscillometric envelope is used to calculate the systolic pressure. Verification of the best fit lines may be made during both passes by constraining the slopes of the lines both absolutely and relative to each other to lie within certain predetermined ranges.

The resulting method for calculating systolic, MAP, and diastolic pressures is less sensitive to erroneous oscillation amplitudes than prior art methods since all points in the area of interest along the oscillometric envelope are weighted equally. Also, a linear approximation to the oscillometric envelope in accordance with the invention allows points from multiple blood pressure determinations to be combined and used in the determination of the best fit lines and hence in the determination of an average blood pressure over a certain time interval. The inventor has also found that this technique may be used to show trends in the oscillometric blood pressure data that are updated at a fast rate using points from fast blood pressure determinations which use large pressure decrementing steps.

BRIEF DESCRIPTION OF THE DRAWINGS

The present invention will be better understood after reading the following detailed description of the presently preferred embodiments thereof with reference to the appended drawings, in which.

DETAILED DESCRIPTION OF THE PRESENTLY PREFERRED EMBODIMENT

A system and method which meets the above-mentioned objects and provides other beneficial features in accordance with the presently preferred exemplary embodiment of the invention will be described below with reference to FIGS. 3 and 4. Those skilled in the art will readily appreciate that the description given herein with respect to those figures is for explanatory purposes only and is not intended in any way to limit the scope of the invention. Also, common reference numbers are used throughout the drawings to represent common elements. All questions regarding the scope of the invention should be resolved by referring to the appended claims.

Figure 1:
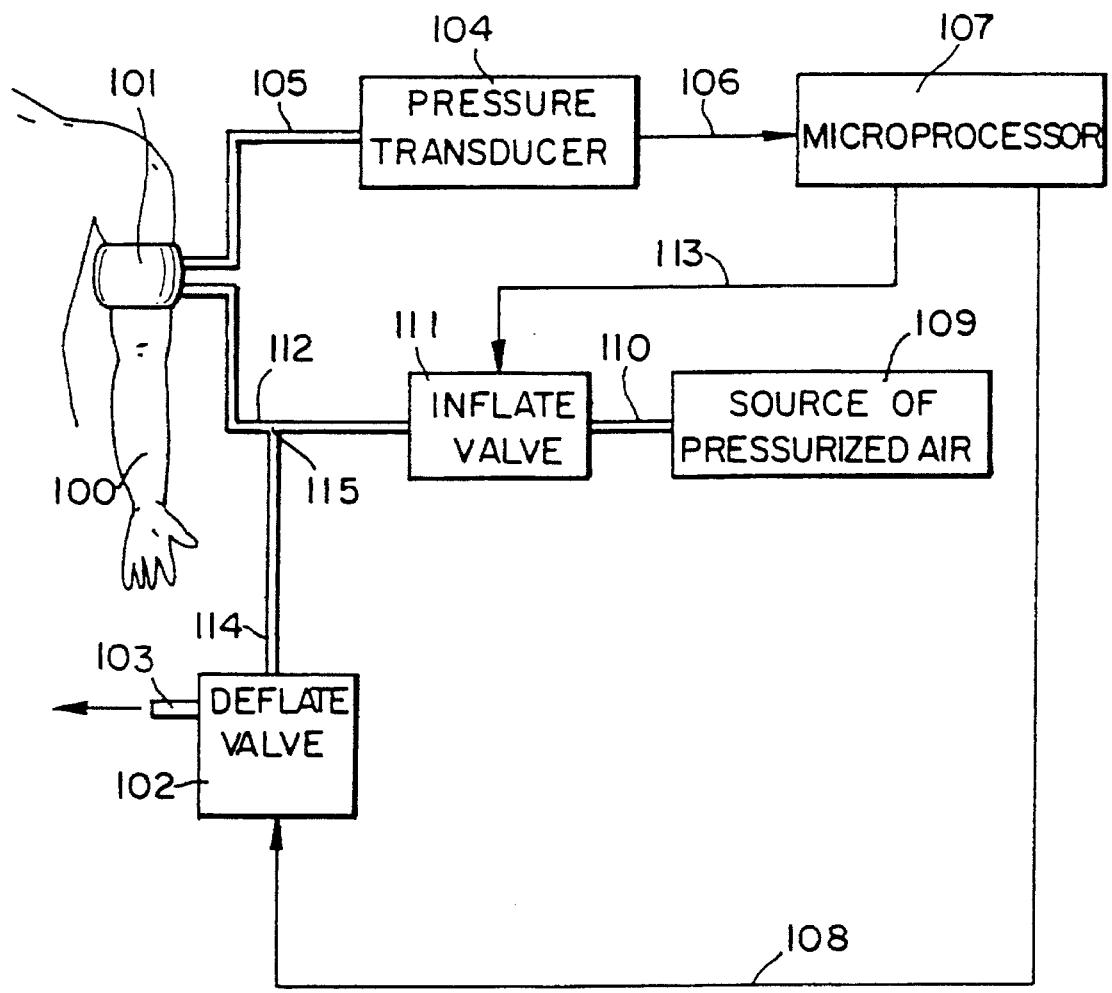
FIG. 1 is a schematic representation of a conventional noninvasive blood pressure ("NIBP") monitor of the type to which the present invention is directed.
Figure 2:
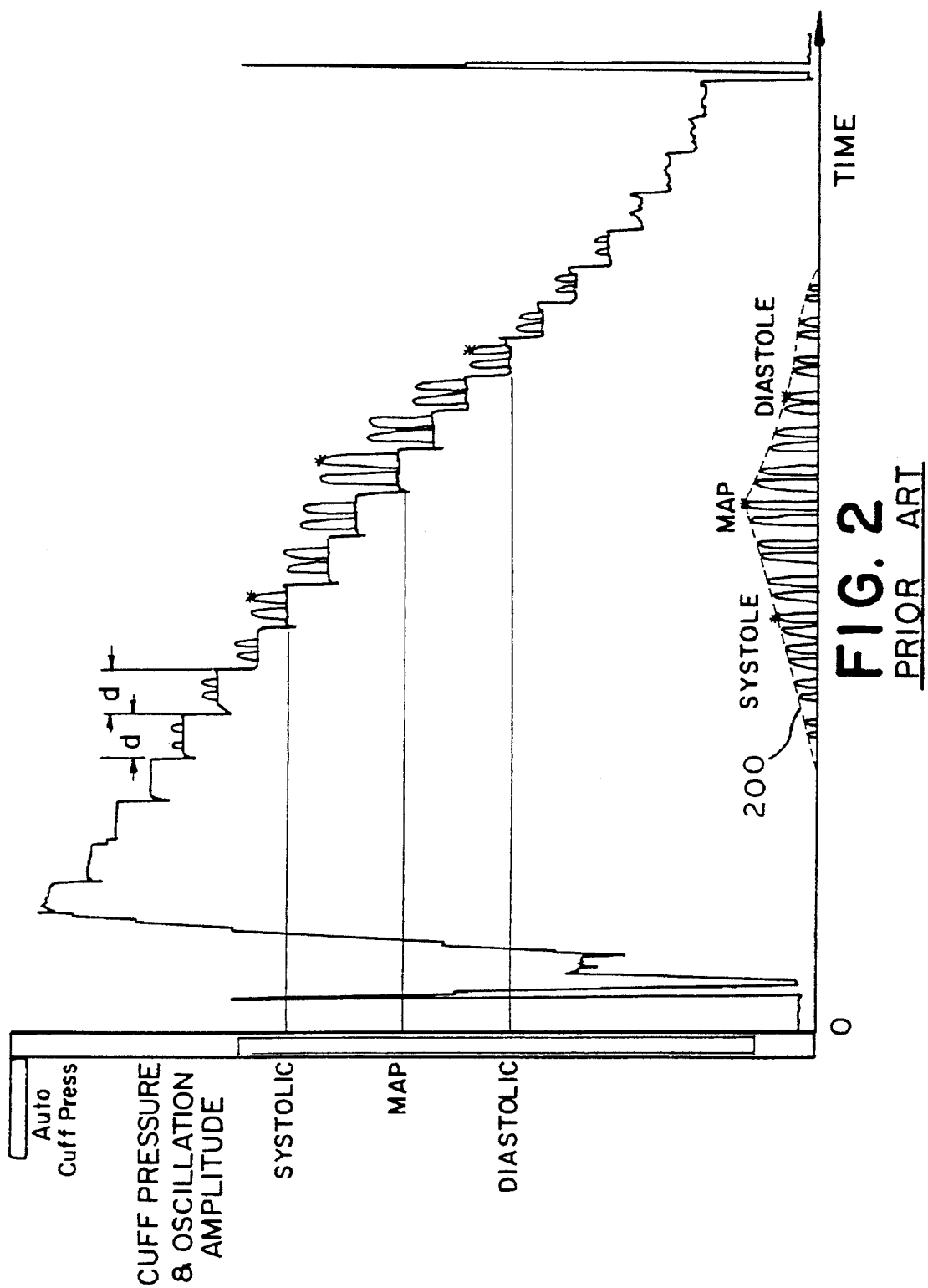
FIG. 2 is a pressure versus time graph illustrating a measuring cycle including step deflation steps and the corresponding oscillation complexes measured using a conventional NIBP monitor.

As noted above with respect to FIGS. 1 and 2, the oscillometric technique for determining blood pressure operates by measuring arterial pulse amplitudes at respective sample cuff pressures. The resulting pulse amplitude samples form an oscillometric envelope 200 from which MAP and the diastolic and systolic pressures may be determined. In accordance with the invention, however, MAP and the diastolic and systolic pressures are determined from the pulse amplitude samples in a different manner using linear approximation techniques. Such techniques in accordance with the invention will be described with respect to FIGS. 3 and 4.

Figure 3A:
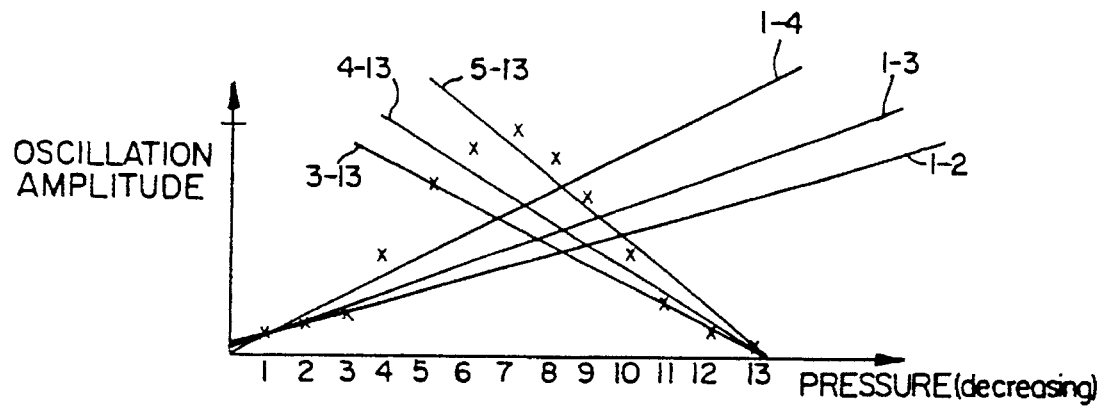
FIGS. 3(a)–3(c) are oscillation amplitude versus pressure curves illustrating the linear approximation technique of the invention.

In FIG. 3(a), the pulse amplitudes of the sample points making up oscillometric envelope 200 are plotted versus decreasing pressure. One of the lines is the best fit line through the points on the low pressure side of the oscillometric envelope 200, while the other line is the best fit line through the points on the high pressure side of the oscillometric envelope 200. The dividing point for the low and high pressure sides is chosen as the point where the best fit line through the points on one side and the best fit line through the points on the other side have the greatest amplitude at the point of intersection. The result is a linear approximation to the oscillometric envelope 200 by two lines forming a triangle with the baseline.

Figure 3B:
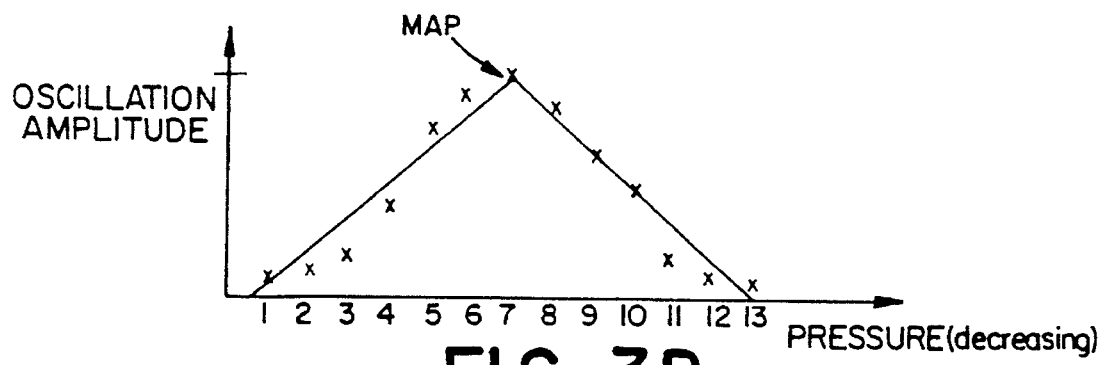

In the example illustrated in FIG. 3(a), 13 pulse amplitudes were taken. In accordance with the invention, a linear approximation to the oscillometric envelope 200 formed by these 13 sample points is formed by first determining the best fit line through sample points starting at one end of the oscillometric envelope 200 (samples 1 and 2) and storing its slope. The best fit line through the remainder of the sample points starting at the other end of the oscillometric envelope 200 (samples 3–13) is also determined, and its slope is stored. The intersection point of the two best fit lines is also determined and stored. This process is repeated by determining the best fit line through sample points 1 through 3 and storing its slope, determining the best fit line through the remainder of the sample points (samples 4–13) and storing its slope, and determining and storing the intersection point of the two best fit lines. This process is repeated until all combinations of adjacent sample points and best fit lines from the respective ends of the oscillometric envelope 200 have been determined, given that at least two points are necessary to form any line. In other words, a first best fit line is calculated for pulse amplitude points x=2 through x=n−2 for the x pulse amplitude points starting at a first end of the oscillometric envelope and a second best fit line is calculated through n−x pulse amplitude points starting at the other end of the oscillometric envelope, where n corresponds to the number of respective cuff pressure levels and it is recognized that at least two points are necessary for forming either of the best fit lines. Several such best fit lines are illustrated in FIG. 3(a). Once all of the intersection points of the best fit lines have been determined and stored, the intersection point with the maximum pulse amplitude is selected as the maximum point of the triangle approximating the oscillometric envelope 200 and is determined to correspond to the mean arterial pressure (MAP). On the other hand, MAP may be determined as some known function of the intersection point with maximum amplitude or may be determined from the area of the resulting triangle. The corresponding triangle approximating the oscillometric envelope 200 is illustrated in FIG. 3(b).

Figure 3C:
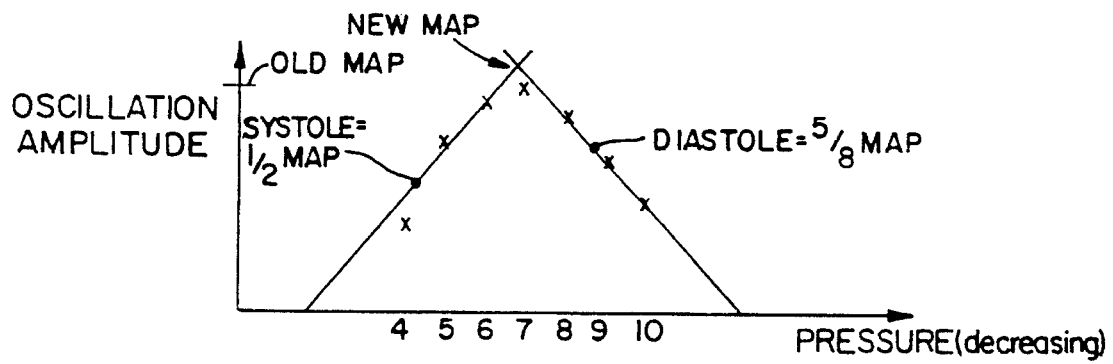

Preferably, a second pass is performed to improve the linear approximation by eliminating points with oscillation amplitudes that are outside of the area of interest (e.g., are at pressures above systolic or below diastolic), such as points that have oscillation amplitudes less than half of the maximum amplitude (MAP) determined in the first pass. Since all points contribute to the slope of the best fit lines, this step is desired to prevent the linear approximation from being distorted by samples which are clearly out of range or otherwise erroneous. The best fit lines are then recalculated from the remaining points in the same manner as described above, and the point with the maximum amplitude for the intersection of the best fit lines (or some function thereof) is then used as MAP and as the maximum amplitude for the determination of the systolic and diastolic pressures. FIG. 3(c) illustrates the resulting triangular approximation to the oscillometric envelope 200, where sample points 1 through 3 and 11 through 13 have been removed from the determination since they have amplitudes less than ½ MAP. In this case, MAP is adjusted slightly upward from the value for MAP determined in the first pass. Of course, subsequent passes may be taken until all remaining samples are within a certain tolerance. Also, verification of the best fit lines may be made during both passes by constraining the slopes of the lines both absolutely and relative to each other to lie within certain predetermined ranges.

The best fit line through the points on the diastolic side of the oscillometric envelope 200 is then used to calculate the diastolic pressure, while the best fit line through the points on the systolic side of the oscillometric envelope 200 is used to calculate the systolic pressure. For example, the diastolic pressure may be calculated as the pressure corresponding to the amplitude on the best fit line on the diastolic side of the oscillometric envelope 200 having a value which is ⅝ the pulse amplitude at MAP. Similarly, the systolic pressure may be calculated as the pressure corresponding to the amplitude on the best fit line on the systolic side of the oscillometric envelope 200 having a value which is ½ the pulse amplitude at MAP. These values can be readily determined from the slope of the best fit lines and are illustrated on the linear approximation to the oscillometric envelope 200 shown in FIG. 3(c).

Figure 4:
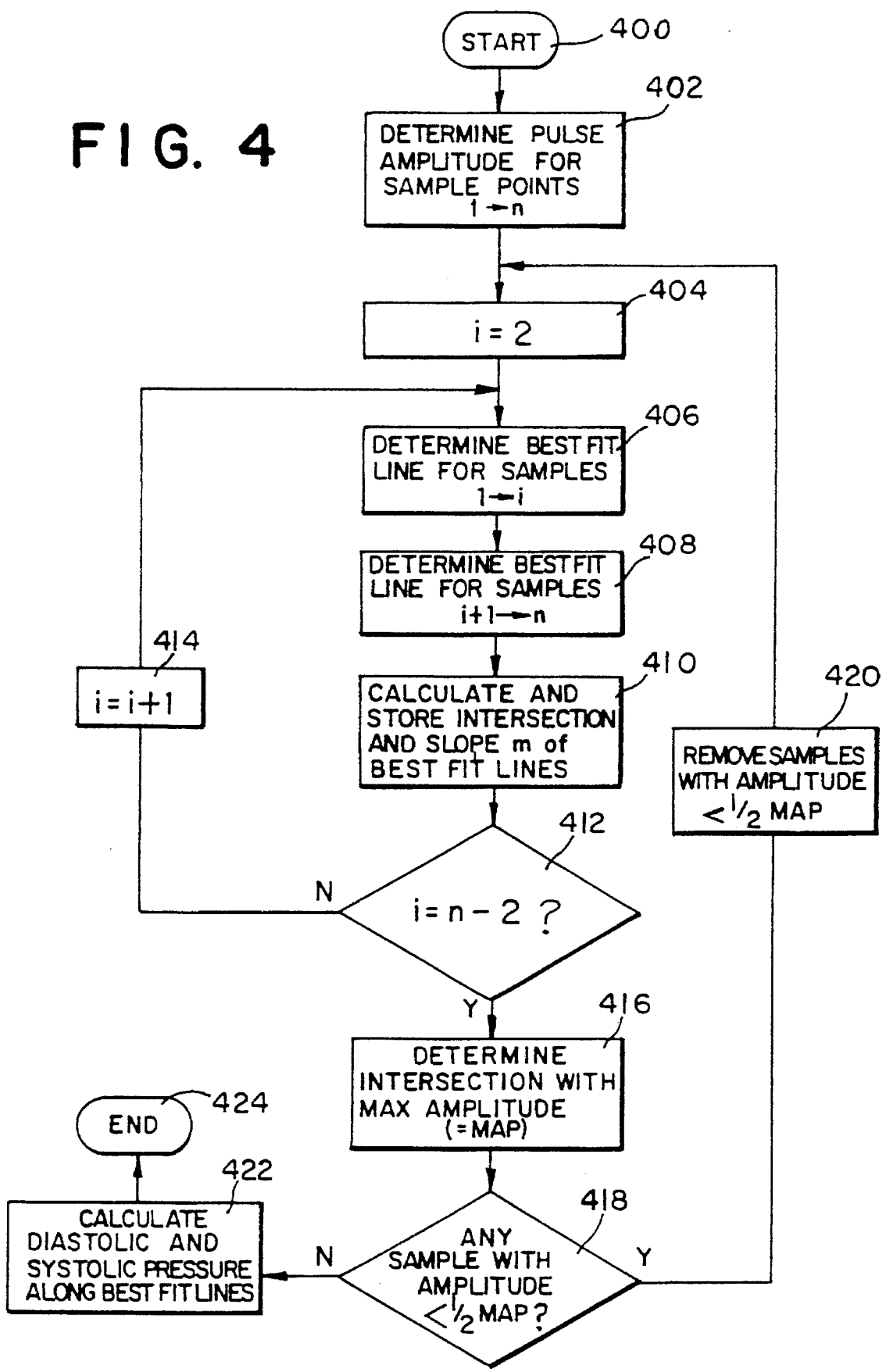
FIG. 4 is a flow chart illustrating the linear approximation technique for determining MAP, diastolic pressure and systolic pressure in accordance with the invention.

A flow chart of a MAP determination algorithm for implementing the linear approximation technique of the invention in the software of microprocessor 107 in accordance with a preferred embodiment is illustrated in FIG. 4. Of course, a dedicated hardware circuit may also be used to implement the illustrated algorithm.

As shown in FIG. 4, the MAP determination algorithm starts at step 400 and determines the pulse amplitude at n respective step deflation/inflation sample pressures using known techniques at step 402. The amplitudes and corresponding pressures for the n sample points are stored for processing. At step 404, an index counter is set to 2 prior to entry into the loop comprising steps 406–412. At step 406, the best fit line for the first two sample points is determined during the first trip through the loop. This best fit line is illustrated as line 1–2 in FIG. 3(a). Then, at step 408, the best fit line for the remaining sample points (samples 3–13) is determined during the first trip through the loop (n=13). This best fit line is illustrated as line 3–13 in FIG. 3(a). At step 410, the intersection point of the resulting best fit lines is calculated and stored along with the respective slopes m of the best fit lines. At step 412, it is determined whether all best fit lines from respective ends of the oscillometric envelope 200 have been determined. Since at least two points are required to identify a line, this is accomplished by determining if best fit lines have been determined for all i, where i<n−2. If i<n−2, index i is incremented at step 414, and the best fit lines for the next combination of sample points from each end of the oscillometric envelope 200 are determined. The loop is exited at step 412 when i=n−2.

Next, the values stored at step 410 are checked at step 416 to determine which intersection point has the maximum pulse amplitude. MAP is determined as the corresponding pressure or as the pressure at some function of the intersection point, such as from the area under the triangle formed by the best fit lines. Processing could stop here. However, it is desirable in a preferred embodiment to eliminate all points which may introduce error into the determination of the best fit lines, such as points with oscillation amplitudes that are outside of the area of interest (e.g., are at pressures above systolic or below diastolic). For example, it is determined at step 418 whether there are any sample points with oscillation amplitudes less than half of the maximum determined in the first pass or, alternatively, outside of a certain tolerance for particular pressures. If so, such sample points are removed at step 420. The best fit lines are then recalculated in steps 404–414 from the remaining points, and the point having the maximum pulse amplitude where the best fit lines intersect (or some function thereof) is again determined at step 416 to correspond to MAP. If it is determined at step 418 that no subsequent passes are necessary to bring all remaining sample points within a certain tolerance, the diastolic and systolic pressures are calculated from MAP and the slopes of the best fit lines at step 422. As noted above, the slope of the best fit line through the points on the diastolic side of the oscillometric envelope 200 is used to calculate the diastolic pressure (pressure on diastolic side of oscillometric envelope 200 where amplitude=⅝ MAP amplitude), while the slope of the best fit line through the points on the systolic side of the oscillometric envelope 200 is used to calculate the systolic pressure (pressure on systolic side of oscillometric envelope 200 where amplitude=½ MAP amplitude). Of course, verification of the best fit lines may be made during both passes by constraining the slopes of the lines both absolutely and relative to each other to lie within certain predetermined ranges. The MAP determination algorithm is then exited at step 424.

The resulting method for calculating systolic, MAP, and diastolic pressures is less sensitive to erroneous oscillation amplitudes than prior art methods since all points in the area of interest along the oscillometric envelope 200 are weighted equally. Also, a linear approximation to the oscillometric envelope 200 in accordance with the invention allows points from multiple blood pressure determinations to be combined and used in the determination of the best fit lines and hence in the determination of an average blood pressure over a certain time interval. In this manner, maximum resolution may be provided in the area of interest on the oscillometric envelope 200. This technique may also be used to show trends in the oscillometric blood pressure data that are updated at a fast rate using points from fast blood pressure determinations which use large pressure decrementing steps.

It will be appreciated by those skilled in the art that the foregoing has set forth the presently preferred embodiment of the invention and an illustrative embodiment of the invention but that numerous alternative embodiments are possible without departing from the novel teachings of the invention. For example, those skilled in the art will appreciate that the techniques of the invention may be used for blood pressure monitors in which the pressure is incremented from diastolic as described, for example, in U.S. Pat. No. 4,461,266 to Hood, Jr. et al. Also, those skilled in the art will appreciate that the techniques of the invention may be used for blood pressure monitors which do not use amplitude matching techniques described by Ramsey to determine whether oscillation complexes of sufficient quality have been received. In addition, those skilled in the art will appreciate that the techniques of the invention may be used in continuous as well as step inflate/deflate type monitors for determining the oscillometric blood pressure. Furthermore, any techniques for determined best fit lines through sample points may be used within the scope of the invention. Accordingly, all such modifications are intended to be included within the scope of the appended claims.

I claim:

1. An automated sphygmomanometer apparatus, comprising:

an inflatable and deflatable pressure cuff;

inflating means operatively coupled to said cuff for selectively applying a medium under pressure to said cuff for inflating and pressurizing said cuff;

cuff pressure sensing means coupled to said cuff for sensing cuff pressure including any arterial blood pressure oscillations therein;

deflating means operatively coupled to said cuff for selectively relieving pressure from said cuff;

control means for controlling said inflating means to inflate said cuff and said deflating means to deflate said cuff to respective cuff pressure levels for the detection of said arterial blood pressure oscillations at each of said respective cuff pressure levels during a blood pressure determination, and for determining an oscillometric envelope comprising pulse amplitude points corresponding to said arterial blood pressure oscillations at said respective cuff pressure levels during said blood pressure determination; and processing means for linearly approximating said oscillometric envelope with a pair of best fit lines and for determining a mean arterial pressure of said patient based on a pressure at a point of intersection of said pair of best fit lines.

2. An apparatus as in claim 1, wherein said processing means calculates said pair of best fit lines as a first line which is a best fit line through pulse amplitude points on a diastolic side of said oscillometric envelope and a second line which is a best fit line through pulse amplitude points on a systolic side of said oscillometric envelope.

3. An apparatus as in claim 2, wherein said processing means excludes from said pulse amplitude points those pulse amplitude points having pulse amplitudes outside of a predetermined range prior to calculating said first and second lines.

4. An apparatus as in claim 2, wherein said processing means calculates diastolic pressure as a pressure corresponding to a point on said first line having a pulse amplitude which is approximately ⅝ of said mean arterial pressure and calculates systolic pressure as a pressure corresponding to a point on said second line having a pulse amplitude which is approximately ½ of said mean arterial pressure.

5. An apparatus as in claim 2, wherein said processing means calculates, for x=2 through x=n−2, a first best fit line through x pulse amplitude points starting with pulse amplitude points at a first end of said oscillometric envelope and a second best fit line through n-x pulse amplitude points starting with pulse amplitude points at a second end of said oscillometric envelope, where n corresponds to the number of said respective cuff pressure levels, calculates and stores pressure and pulse amplitude values for intersection points of said first and second best fit lines, and selects as said first and second lines those best fit lines having an intersection point with each other at a maximum pulse amplitude.

6. A method of measuring blood pressure of a patient using an automatic oscillometric blood pressure monitor comprising a cuff, means for inflating and deflating said cuff to respective cuff pressure levels during a blood pressure measurement, means for measuring arterial blood pressure oscillation complexes at said respective cuff pressure levels through measurement of time varying pressures within said cuff, and means for searching for arterial blood pressure oscillation complexes at said respective cuff pressure levels, said method comprising the steps of:

selectively inflating and deflating said cuff and outputting a cuff pressure signal at a plurality of cuff pressure levels so as to form an oscillometric envelope comprising pulse amplitude points corresponding to said arterial blood pressure oscillations at said plurality of cuff pressure levels;

determining a linear approximation to said oscillometric envelope as a pair of best fit lines through said pulse amplitude points; and determining a mean arterial pressure of said patient based on a pressure at a point of intersection of said pair of best fit lines.

7. A method as in claim 6, wherein said linear approximation determining step comprises the step of calculating said pair of best fit lines as a first line which is a best fit line through pulse amplitude points on a diastolic side of said oscillometric envelope and a second line which is a best fit line through pulse amplitude points on a systolic side of said oscillometric envelope, and said mean arterial pressure determining step comprises the step of determining a point of intersection of said first and second lines.

8. A method as in claim 7, comprising the further step of excluding from said pulse amplitude points those pulse amplitude points having pulse amplitudes outside of a predetermined range, prior to said linear approximation determining step.

9. A method as in claim 7, comprising the further steps of calculating diastolic pressure as a pressure corresponding to a point on said first line having a pulse amplitude which is approximately 5/8 of said mean arterial pressure and calculating systolic pressure as a pressure corresponding to a point on said second line having a pulse amplitude which is approximately 1/2 of said mean arterial pressure.

10. A method as in claim 7, wherein said linear approximation determining step comprises the steps of calculating, for x=2 through x=n−2, a first best fit line through x pulse amplitude points starting with pulse amplitude points at a first end of said oscillometric envelope and a second best fit line through n-x pulse amplitude points starting with pulse amplitude points at a second end of said oscillometric envelope, where n corresponds to said predetermined number of cuff pressure levels, calculating and storing pressure and pulse amplitude values for intersection points of said first and second best fit lines, and selecting as said first and second lines those best fit lines having an intersection point with each other at a maximum pulse amplitude.

* * * * *